United States Patent [19]
Yoshimoto et al.

[11] Patent Number: 5,633,111
[45] Date of Patent: May 27, 1997

[54] PHOTORESIST COMPOSITION AND ARTICLE CONTAINING 1,2-QUINONEDIAZIDE AND AN ORGANIC PHOSPHOROUS ACID COMPOUND

[75] Inventors: Hiroshi Yoshimoto; Kesanao Kobayashi, both of Shizuoka, Japan

[73] Assignee: Fuji Photo Film Co., Ltd., Kanagawa, Japan

[21] Appl. No.: 969,565

[22] Filed: Oct. 30, 1992

[30] Foreign Application Priority Data

Nov. 1, 1991 [JP] Japan ................. 3-287899
Jan. 31, 1992 [JP] Japan ................. 4-016232

[51] Int. Cl.⁶ .......................... G03F 7/023; G03C 1/61
[52] U.S. Cl. .................. 430/165; 430/191; 430/192; 430/271.1; 430/272.1; 430/275.1; 430/277.1; 430/278.1
[58] Field of Search .......................... 430/165, 177, 430/191, 192, 196, 270.1, 271.1, 272.1, 275.1, 277.1, 278.1

[56] References Cited

U.S. PATENT DOCUMENTS

| | | | |
|---|---|---|---|
| 3,404,003 | 10/1968 | Steppan. | |
| 4,963,463 | 10/1990 | Koshiba et al. | 430/191 |
| 4,968,582 | 11/1990 | Tranjan et al. | 430/270 |
| 5,114,827 | 5/1992 | Tranjan et al. | 430/271 |
| 5,143,814 | 9/1992 | Pampalone | 430/191 |
| 5,213,941 | 5/1993 | Platzer | 430/191 |

FOREIGN PATENT DOCUMENTS

| | | |
|---|---|---|
| 6088942 | 5/1985 | Japan. |
| 63276047 | 11/1988 | Japan. |
| 2222951 | 9/1990 | Japan. |
| 1502015 | 2/1978 | United Kingdom. |

*Primary Examiner*—Christopher G. Young
*Attorney, Agent, or Firm*—Sughrue, Mion, Zinn, Macpeak & Seas

[57] ABSTRACT

A positive type or negative type photoresist composition for fine processing having excellent resolution, sensitivity, adhesive-ness and developability comprising:

(a) an alkali soluble resin or a resin having anti-alkali dissolution groups in the molecules thereof, (b) a light-sensitive compound, and (c) at least one organic compound selected from the group consisting of organic phosphorus acid compounds and esters thereof in an amount of 0.001 to 10% by weight based on a weight of the resin. In addition, the present invention is directed to an etching method utilizing the positive type or negative type photoresist composition.

21 Claims, No Drawings

PHOTORESIST COMPOSITION AND ARTICLE CONTAINING 1,2-QUINONEDIAZIDE AND AN ORGANIC PHOSPHOROUS ACID COMPOUND

FIELD OF THE INVENTION

The present invention relates to a photoresist which is sensitive to radial rays, more specifically to a positive type or negative type photoresist composition for fine processing comprising an alkali soluble resin and a light-sensitive compound such as a 1,2-quinonediazide compound, an azide compound or a photo acid generating agent wherein the photoresist composition has excellent resolution, sensitivity, adhesiveness and developability.

BACKGROUND OF THE INVENTION

The typical application fields of a photoresist are the manufacturing of a circuit substrate such as IC, and other photofabrication steps. The photoresist is coated on a substrate such as a semiconductor wafer, glass, ceramics, ITO, and metal by a spin coating method or a roller coating in a thickness of 0.3 to 3 µm and then the coated substrate is heated for drying and a circuit pattern is printed thereon via an exposure mask by irradiation of UV rays, followed by developing, whereby a negative or positive image can be obtained. Further, etching is carried out using this image as a mask to provide a substrate with patternwise processing.

There is generally used as a positive type photoresist composition, a composition containing an alkali soluble resin and a naphthoquinonediazide compound as a light-sensitive substance. For example, there are described a novolak type phenol resin/a naphthoquinonediazide-substituted compound in U.S. Pat. Nos. 3,666,473, 4,115,128 and 4,173,470, and the example of a novolak resin consisting of cresol-formaldehyde/trihydroxybenzophenone-1,2-naphthoquinonediazide sulfonic acid ester as the most typical composition in "Introduction to Microlithography" written by L. F. Thompson (ACS Publication, No. 219, pp. 112 to 121).

In such a positive type photoresist fundamentally consisting of a novolak resin and a quinonediazide compound, the novolak resin can be dissolved in an alkaline aqueous solution without swelling and the naphthoquinonediazide compound acts as an anti-dissolution agent. Characteristically, naphthoquinonediazide loses its anti-dissolution capability and alkali solubility of the novolak resin increases when naphthoquinonediazide is subjected to light irradiation to generate carboxylic acid.

From this view-point, many of the positive type photoresists containing the novolak resin and naphthoquinonediazide type light-sensitive material have so far been developed and put into practical use, and sufficient results have been obtained in line width processing of not much more than 0.8 to 2 µm.

Meanwhile, a composition containing an alkali soluble resin and an azide compound as a light-sensitive material is used as a negative type photoresist composition. There are published "a phenol resin/azide compound" resist in A series of azide-phenolic resin resists for the range of deep UV to visible light, Proc. SPIE, by S. Koibuchi et al, vol. 539, pp. 182 (1985), and "a polyvinyl phenol resin/azide compound" resist in Azide-phenolic resin resists sensitive to visible light, Proc. SPIE, by S. Nonogaki et al, vol. 539, pp. 189 (1985).

Such negative type photoresist fundamentally consisting of an alkali soluble resin and an azide compound can be dissolved in an alkaline aqueous solution with no swelling of the alkali soluble resin, and the azide compound generates nitrene (–N̈:) by light irradiation to act as a photo crosslinking agent or a photo addition agent.

A chemical sensitization series resist composition containing a photo acid generating agent is described in U.S. Pat. Nos. 410,201 and 873,914. The chemical sensitization series resist composition is a pattern forming material in which acid is generated in an exposed portion by irradiation of radial rays such as far ultraviolet rays, and the solubilities of an irradiated portion and a non-irradiated portion to a developing solution are changed by the reaction in which this acid is used as a catalyst to form a pattern on a substrate.

A positive type chemical sensitization series resist can be roughly classified as (1) a three components system comprising an alkali soluble resin, a compound, generating acid (a photo acid generating agent) by exposure to radial rays, and an anti-dissolution compound, and (2) a two component system comprising a resin having a group which becomes alkali soluble by a reaction with acid and a photo acid generating agent.

A negative type chemical sensitization series resist can be roughly classified as (1) a three components system comprising an alkali soluble resin, a compound, generating acid (a photo acid generating agent) by exposure to radial rays, and an acid crosslinking agent, and (2) a two component system comprising a resin having a group which becomes alkali insoluble by a reaction with acid and a photo acid generating agent.

Also, the example of "a phenol resin series acid catalyst crosslinking type negative type resist" is described in Acid-Catalyzed Cross-Linking in Phenolic-Resin-Based Negative Resists, by A. K. Berry et al (ACS Publication, No. 412, pp. 86 to 99) as the most typical composition.

In general, a photoresist in which an alkali soluble resin is contained as a primary component has a markedly excellent resolution compared with the other rubber series negative type resist, and is utilized for high resolution as an etching protective layer in preparing an integrated circuit such as IC, LSI and a gate electrode of a liquid crystal display.

In recent years, a substrate processing technique in which a dry etching method is used in keeping with a fineness due to a high integration of a integrated circuit has been used. In the art, however, fine processings of several µm are carried out by a wet etching method having merit in terms of equipment price and throughput. Further, there has come to be carried out a substrate processing technique in which a dry etching method and a wet etching method are combined in order to prevent electrostatic destruction of the element. In fine processing by such a wet etching method, adhesiveness of a resist layer to the substrate is very important in addition to the resolution. That is, resist patterns of about 1 to 3 µm in a substrate processed only by a wet etching method and about 0.5 to 1 µm in a substrate processed by a dry etching method and a wet etching method are requested so as to strongly adhere the resist pattern on a substrate without peeling off from the substrate through development and wet etching. A conventional photoresist is not generally satisfactory in adhesiveness and an improvement thereof is desired.

SUMMARY OF THE INVENTION

An object of the present invention is to provide a photoresist composition having a high adhesiveness to a substrate and capable of reproducing a fine pattern even with a wet etching method and an etching method used therewith.

The intensive investigations made by the present inventors has resulted in finding that the adhesiveness of a resist to a substrate is markedly improved by adding at least one of organic phosphorus acid compound and esters thereof to the photoresist.

That is, an object of the present invention has been achieved by a positive type or negative type photoresist composition containing:

(a) an alkali soluble resin or a resin having an anti-alkali dissolution group, (b) a light-sensitive compound, and (c) at least one of organic phosphorus acid compounds and esters thereof in an amount of 0.001 to 10% by weight based on the weight of the resin (a).

In addition, the present invention provides an etching method comprising the steps of coating a photoresist composition on a substrate, developing the photoresist after it has seen subjected to patternwise exposure and subjecting the substrate with a pattern as a resist to wet etching, wherein the photoresist composition contains the positive type or negative type photoresist composition, defined immediately above.

DETAILED DESCRIPTION OF THE INVENTION

The present invention will be explained below in detail.

A light-sensitive composition containing organic acid is disclosed in JP-A-60-88942 (the term "JP-A", as used herein, means an unexamined published Japanese patent application) but it does not meet the object of the present invention since the object of the above invention is to obtain a sharp image immediately after exposing. Because of this, in the above invention, it is an essential constitutional requisite to contain a discoloring agent the color tone of which is changed by an interaction with a photodecomposition product. In the present invention, however, the discoloring agent may be contained as long as it does not adversely affect the performance of the photoresist. In addition, in the present invention, the discoloring agent is not an essential constitutional requisite.

Examples of the alkali soluble resin used in the present invention include a novolak resin, an acetone-pyrogallol resin, polyhydroxystyrene, a styrene-maleic acid anhydride copolymer, modified polysilsesquioxane modified to an alkali soluble type by a Friedel-Crafts reaction, and a carboxyl group-containing methacrylate series resin, a derivative thereof and a mixture thereof, but the present invention is not limited thereto.

Furthermore, examples of the resin having anti-alkali dissolution groups in the molecules thereof include t-butoxycarbonyloxystyrene polymer, t-butoxycarbonyloxy-α-methylstyrene polymer and a mixture thereof. These resins becomes alkali soluble resin by, for example, an action of the acid generated from a photo acid generating agent.

In the present invention it is preferred to use 1,2-quinonediazide compound, an azide compound or a photo-acid generating compound as a light-sensitive agent.

Examples of the 1,2-quinonediazide compound used in the present invention include an ester of 1,2-naphthoquinonediazide-5-sulfonic acid, 1,2-naphthoquinonediazide-4-sulfonic acid, or 1,2-benzoquinonediazide-4-sulfonic acid and a polyhydroxy aromatic compound. A partially esterized polyhydroxy compound and a mixture of two or more of these diazide compounds can also be used.

Examples of the polyhydroxy aromatic compound include polyhydroxybenzophenones such as 2,3,4-trihydroxybenzophenone, 2,4,4'-trihydroxybenzophenone, 2,4,6-trihydroxybenzophenone, 2,3,4,4'-tetrahydroxybenzophenone, 2,2',4,4'-tetrahydroxybenzophenone, and 2,4,6,3',4',5'-hexahydroxy-benzophenone; polyhydoxyphenylalkyl ketones such as 2,3,4-trihydroxyacetophenone and 2,3,4-trihydroxyphenyl hexyl ketone; bis[(poly)hydroxyphenyl] alkanes such as bis(2,4-dihydroxyphenyl) methane, bis(2,3,4-trihydroxyphenyl) methane, and bis(2,4-dihydroxyphenyl) propane; polyhydroxybenzoic acid eters such as propyl 3,4,5-trihydroxybenzoate and phenyl 3,4,5-trihydroxybenzoate; bis(polyhydroxybenzoyl) alkanes or bis (polyhydroxy-benzoyl) aryl compounds such as his (2,3,4-trihydroxybenzoyl) methane, and bis(2,3,4-trihydroxybenzoyl) benzene, respectively; alkylene-di (polyhydoxybenzoates) such as ethylene glycol-di(3,5-dihydroxy-benzoate; polyhydoxybiphenyls such as 3,5,3',5'-biphenyltetrol, 2,4,2',4'-biphenyltetrol, 2,4,6,3',5'-biphenylpentol, and 2,4,6,4',6'-biphenylhexol; polyhydroxytriphenylmethanes such as 4,4',3",4"-tetrahydroxy-3,5,3',5'-tetramethyltriphenylmethane, 4,4',2", 3",4"-pentahydroxy-3,5,3',5'-tetramethyl-triphenylmethane, and 2,3,4,2',3',4',3",4"-octahydroxy-5,5'-diacetyltriphenylmethane; polyhydroxyspirobi-indanes such as 3,3,3',3'-tetramethyl-1,1'-spirobi-indane-5,6,5',6'-tetrol, 3,3,3',3'-tetramethyl-1,1'-spirobi-indane-5,6,7,5',6',7'-hexol, 3,3,3',3'-tetramethyl-1,1'-spirobi-indane-4,5,6,4',5',6'-hexol, and 3,3,3',3'-tetramethyl-1,1'-spirobi-indane-4,5,6,5', 6',7'-hexol; and novolak resins.

In the present invention, the ratio of the 1,2-quinonediazide compound to the alkali soluble resin may be 5 to 100 parts by weight, preferably 10 to 50 parts by weight of the 1,2-quinonediazide compound per 100 parts by weight of the resin. A ratio of less than 5 parts by weight tends to lower the residual layer rate and a ratio exceeding 100 parts by weight reduces the sensitivity and solubility in a solvent.

Examples of the azide compound which may be used in the present invention include: 4,4'-diazidechalcone, 2,6-bis (4'-diazidebenzal)-4-methylcyclohexanone, 2,2-bis(4'-azidephenyl) propane, 4,4'-diazidephenyl ether, 3-(azidestyryl)-5,5-dimethyl-2-cyclohexene-1-one, and 3-[4-(azidephenyl)-1,3-butadienyl]-5,5-dimethyl-2-cyclohexene-1-one.

In the present invention, the ratio of the azide compound to the alkali soluble resin may be 5 to 100 parts by weight, preferably 10 to 60 parts by weight of the azide compound to 100 parts by weight of the resin. A ratio of less than 5 parts by weight tends to lower the residual layer rate and sensitivity, and a ratio exceeding 100 parts by weight reduces the solubility in a solvent.

Where an anti-alkali dissolution compound other than an azide compound, such as 1,2-quinonediazide and a compound having a t-butoxycarbonyl group or a t-butylester group is used, there is usually obtained a so-called positive type pattern image in which a portion having no irradiation of an ionizing radiation is formed as an image. Also in this case, however, it is possible as well to carry out a so-called image reversal to effectively obtain a negative pattern by a method in which thermal treatment is carried out in an amine atmosphere, as described in JP-A-63-316429, or by incorporating the compounds such as 2,6-di-t-butylpyridine, benzimidazole, pyridine, quinoline, acridine, lutidine, 1-methylbenzimidazole, and melamineformaldehyde alkyl ether, each described in JP-A-62-35350 and EP263434A, into the resin composition of the present invention.

There can be suitably selected and used as the compound which is decomposed by active rays or radial rays to generate acid, a photopolymerization initiator for a cationic photopolymerization, a photopolymerization initiator for a radical photopolymerization, a photo decoloring agent for dyes, a photo discoloring agent, and conventional compounds which generate acids by rays and the derivatives thereof, which are used for a microresist.

Examples include the diazonium salts described in Photogr. Sci. Eng., by S. I. Schlesinger, 18, 387 (1974), and Polymer, by T. S. Bal et al, 21, 423 (1980); the ammonium salts described in U.S. Pat. Nos. 4,069,055, 4,069,056, and Re. No. 27,992, and Japanese Patent Application-3-140140; the phosphonium salts described in Macromolecules, by D. C. Necker et al, 17, 2468 (1984), Teh, Proc. Conf. Rad. Curing ASIA, by C. S. Wen et al, pp. 478, Tokyo (October 1988), and U.S. Pat. Nos. 4,069,055 and 4,069,056; the iodonium salts described in Macromolecules, by J. V. Crivello et al, 10 (6), 1307 (1977), Chem. & Eng. News, Nov., 28, pp. 31 (1988), European Patent 104,143, U.S. Pat. Nos. 339,049 and 410,201, and JP-A-2-150848 and 2-296514; the sulfonium salts described in Polymer J., by J. V. Crivello et al, 17, 73 (1985), J. Org. Chem., by J. V. Crivello et al, 43, 3055 (1978), J. Polymer Sci., Polymer Chem. Ed., by W. R. Watt et al, 22, 1789 (1984), Polymer Bull., by J. V. Crivello et al, 14, 279 (1985), Macromolecules, by J. V. Crivello et al, 14 (5), 1141 (1981), J. Polymer Sci., Polymer Chem. Ed., by J. V. Crivello et al, 17, 2877 (1979), European Patents 370,693, 3,902,114, 233,567, 297,443, and 297,442, U.S. Pat. Nos. 4,933,377, 161,811, 410,201, 339,049, 4,760,013, 4,734,444, and 2,833,827, and German Patents 2,904,626, 3,604,580, and 3,604,581; the selenonium salts described in Macromolecules, by J. V. Crivello et al, 10 (6), 1307 (1977), and J. Polymer Sci., Polymer Chem. Ed., by J. V. Crivello et al, 17, 1047 (1979); the onium salts such as the arsonium salts described in Teh, Proc. Conf. Rad. Curing ASIA, by C. S. Wen et al, 478, Tokyo (October 1988); the organic halogenated compounds described in U.S. Pat. No. 3,905, 815, JP-B-46-4605 (U.S. Pat. No. 3,579,343; the term "JP-B", as used herewith, means an examined Japanese patent publication), and JP-A-48-36281 (U.S. Pat. No. 3,854,475), JP-A-55-32070 (U.S. Pat. No. 4,258,123), JP-A-60-239736, JP-A-61-169835, JP-A-61-169837, JP-A-62-58241 (U.S. Pat. No. 4,772,534), JP-A-62-212401, JP-A-63-70243, and JP-A-63-298339; the organic metal/organic halogenated compounds described in J. Rad. Curing, by K. Meier et al, 13 (4), 26 (1986), Inorg. Chem., by T. P. Gill et al, 19, 3007 (1980), Acc. Chem. Res., by D. Astruc, 19 (12), 377 (1896), and JP-A-2-161445; the photo acid generating agents having an o-nitrobenzyl type protective group, described in J. Polymer Sci., by S. Hayase et al, 25, 753 (1987), J. Polymer Sci., Polymer Chem. Ed., by E. Reichmanis et al, 23, 1 (1985), J. Photo-chem., by Q. Q. Zhu et al, 36, 85, 39 and 317 (1987), Tetrahedron Lett., by B. Amit et al, (24) 2205 (1973), J. Chem. Soc., by D. H. R. Barton et al, 3571 (1965), J. Chem. Soc., Perkin I, by P. M. Collins et al, pp. 1695 (1975), Tetrahedron Lett., by M. Rudinstein et al, (17), 1445 (1975), J. Am. Chem. Soc., by J. W. Walker et al, 110, 7170 (1988), J. Imaging Technol., by S. C. Busman et al, 11 (4), 191 (1985), Macromolecules, by H. M. Houlihan et al, 21, 2001 (1988), J. Chem. Soc., Chem. Commun., by P. M. Colloins et al, 532 (1972), Macromolecules, by S. Hayase et al, 18, 1799 (1985), J. Electrochem. Soc., Solid State Sci. Technol., by E. Reichmanis et al, 130 (6), Macromolecules, by F. M. Houlihan et al, 21, 2001 (1988), European Patents 0290,750, 046,083, 156,535, 271,851, and 0,388,343, U.S. Pat. Nos. 3,901,710 and 4,181,531, and JP-A-60-198538 and JP-A-53-133022 (G.B. Patent 1,575,281); the compounds which are subjected to a photodecomposition to generate sulfonic acid, represented by iminosulfonate, described in Polymer Preprints Japan, by M. Tunooka et al, 35 (8), J. Rad. Curing, by G. Berner et al, 13 (4), Coating Technol., by M. J. Mijs et al, 55 (697), 45 (1983), Polymer Preprints, Japan, by Akzo, H. Adachi et al, 37 (3), European Patents 0199,672, 84515, 199,672, 044,155, and 0101,122, U.S. Pat. Nos. 618,564, 4,371,605, and 4,431,774, and JP-A-64-18143, JP-A-2-245756 (U.S. Pat. No. 5,118,582), and Japanese Patent Application-3-140109; and the disulfone compounds described in JP-A-61-166544.

Further, compounds in which these groups or compounds each generating acid by rays are introduced into a primary chain or a side chain of a polymer can be used; for example, the compounds described in J. Am. Chem. Soc., by M. E. Woodhouse et al, 104, 5586 (1982), J. Imaging Sci., by S. P. Pappas et al, 30 (5), 218 (1986), Makromol. Chem., Rapid Commun., by S. Kondo et al, 9, 625 (1988), Makromol. Chem., by Y. Yamada et al, 152, 153, 163 (1972), J. Polymer Sci., Polymer Chem. Ed., by J. V. Crivello, 17, 3845 (1979), U.S. Pat. No. 3,849,137, German Patent 3914407, and JP-A-63-26653, JP-A-55-164824 (U.S. Pat. No. 4,576,902), JP-A-62-69263, JP-A-63-146038, JP-A-63-163452 (U.S. Pat. No. 4,857,437), JP-A-62-153853 (U.S. Pat. Nos. 4,822, 716 and 5,017,453), and JP-A-63-146029.

Further, can be used as compounds generating acid by rays described in Synthesis, by V. N. R. Pillai, (1), 1 (1980), Tetrahedron Lett., by A. Abad et al, (47), 4555 (1971), J. Chem. Soc., by D. H. R. Barton et al, (C), 329 (1970), U.S. Pat. No. 3,779,778, and European Patent 126,712.

Typical examples of the photo acid generating agent can be represented by formuale (I) to (VI).

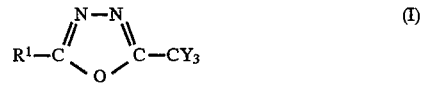

(I)

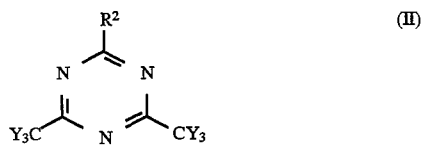

(II)

wherein $R^1$ represents a substituted or unsubstituted aryl or alkenyl group, $R^2$ represents a substituted or unsubstituted aryl, alkenyl or alkyl group, or $-CY_3$, and $Y_3$ represents a chlorine atom or a bromine atom.

(III)

(IV)

wherein $Ar^1$ and $Ar^2$ each represents a substituted or unsubstituted aryl group. Preferred examples of the substituent include an alkyl group, a haloalkyl group, a cycloalkyl group, an aryl group, an alkoxy group, a nito group, a carboxyl group, an alkoxycarbonyl group, a hydroxy group, a mercapto group and a halogen atom.

$R^3$, $R^4$, and $R^5$ each represents a substituted or unsubstituted alkyl or aryl group, preferably an aryl group having 6 to 14 carbon atoms, an alkyl group having 1 to 8 carbon atoms and substituted derivatives thereof. Preferred examples of the substituents for the aryl group include an alkoxy group having 1 to 8 carbon atoms, an alkyl group having 1 to 8 carbon atoms, a nitro group, a carboxyl group, a hydroxy group, and a halogen atom. Preferred examples of the substituents for the alkyl group include an alkoxy group having 1 to 8 carbon atoms, a carboxyl group, and a alkoxycarbonyl group having 2 to 8 carbon atoms.

$Z^-$ represents an anion, such as $BF_4^-$, $A_sF_6^-$, $PF_6^-$, $SbF_6^-$, $SiF_6$, $ClO_4^-$, $CF_3SO_3^-$, $BPh_4^-$ (ph: phenyl group), a condensed polynuclear aromatic sulfonate anion such as a naphthalene-1-sulfonate anion, anthraquinone sulfonate anion, and a dye having a sulfonic acid group, but in the present invention the anion is not limited thereto.

Two groups among $R^3$, $R^4$ and $R^5$, and $Ar^1$ and $Ar^2$ may be combined through each of single bonds or each of the substituents thereof.

The onium salts represents by formlae (III) and (VI) ae well known compounds. They can be synthesized by a method disclosd in, for example, J. W. Knapczyk et al, *J. Am. Chem. Soc.*, 91, 145 (1969), A. L. Maycok et al, *J. Org. Chem.*, 35, 2532 (1970), E. Goethas et al, *Bull. Soc. Chem. Belg.*, 73, 546 (1964), H. M. Leicester, J. Am. Soc., 51, 3587 (1929), J. V. Crivello et al, *J. Polymer Chem.* Ed., 18, 2677 (1980), U.S. Pat. Nos. 2,807,648 and 4,247,473 and JP-A-53-101,331.

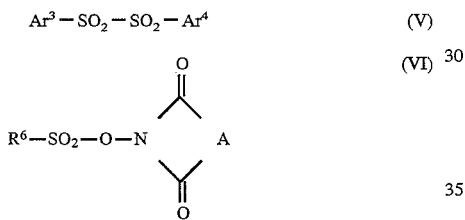

wherein $Ar^3$ and $Ar^4$ each represents a substituted or unsubstituted aryl group, $R^6$ represents a substituted or unsubstituted alkylene, alkenylene or arylene group.

Typical examples of photo acid generating agent desclosed above are shown below.

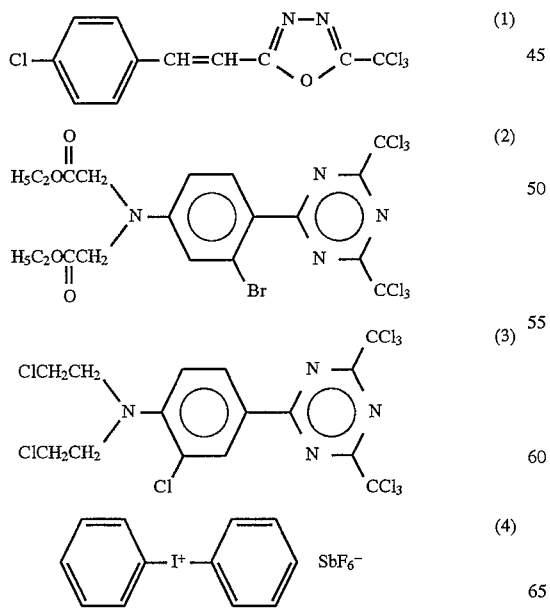

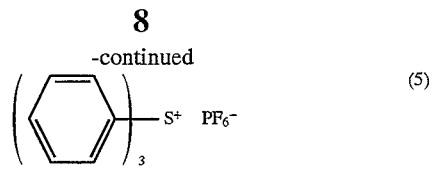

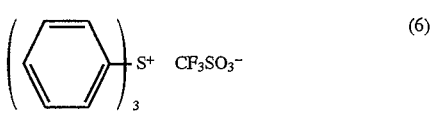

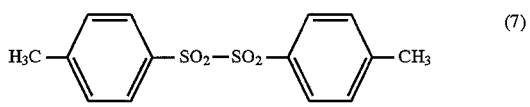

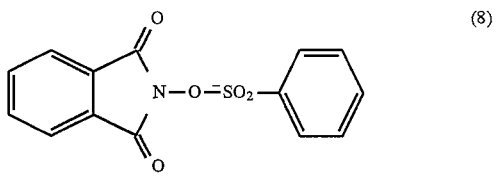

Two or more of photo acid generating agent may be used in combination in the photoresist composition of the present invention.

In the present invention, the ratio of the photo acid generating agent to the resin (a) may be 0.001 to 40 parts by weight, preferably 0.1 to 20 parts by weight of the photo acid generating agent per 100 parts by weight of the resin. A ratio of less than 0.001 part by weight tends to lower the sensitivity and a ratio exceeding 40 parts by weight tends to reduce the solubility in a solvent.

Examples of the anti-dissolution compound which is used in combination with a photo acid generating agent in the photoresist composition include 1-adamantanmethylbenzoate, 1, 2, 4-tris(adamantanmethyl) benzoate, 1, 2, 4, 5-tetrakis(adamantanmethyl)benzoate, and p-(1-adamantanmethyl)toluensulfonate, di-t-butylterephthalate and 4-t-butoxy-p-biphenyl.

The anti-dissolution compound is incorporated into the photoresist composition in an amount of 0.5 to 40 parts by weight based on 100 parts by weight of the alkali-soluble resin.

The organic phosphorus acid compound used in the present invention includes, for example, an organic phosphoric acid compound, and organic phosphorous acid compound, an organic phosphonic acid compound and an organic phosphinic acid compound. Esters of these compounds may also be used. Two or more of these compounds may be used in combination.

The organic phosphorus acid compound and esters thereof used in the present invention is preferably at least one compound selected from the substituted or unsubstituted aliphatic or aromatic compounds represented by formula (I) or formula (II).

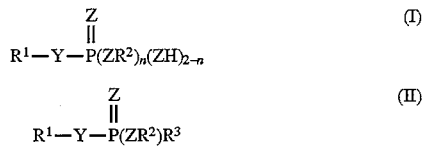

wherein n represents 1 or 2, $R^1$ represents a substituted or unsubstituted alkyl group preferably having 1 to 14 carbon atoms, a substituted or unsubstituted alkoxy group preferably having 1 to 14 carbon atoms, a substituted or unsubstituted aryl group preferably having 6 to 10 carbon atoms, a substituted or unsubstituted aryloxy group preferably having 6 to 10 carbon atoms, a substituted or unsubstituted acyl group preferably having 2 to 14 carbon atoms, or a substituted or unsubstituted acyloxy group preferably having 2 to 14 carbon atoms. $R^2$ and $R^3$ each represents a hydrogen atom or a substituted or unsubstituted alkyl group preferably having 1 to 14 carbon atoms, a substituted or unsubstituted aryl group preferably having 6 to 10 carbon atoms, a substituted or unsubstituted acyl group preferably having 2 to 14 carbon atoms, Y represents a single bond, an oxygen atom or a sulfur atom, and Z represents an oxygen atom or a sulfur atom. These compound may be used in a form of a salt of a metal such as alkali metals e.g., potassium, sodium and lithium, calcium, cobalt, iron, nickel, manganese, magnesium, barium and copper, or a salt of ammonium.

Examples of the organic phosphorus compound represented by formula (I) include phenylphosphonic acid, phenylphosphoric acid, naphthylphosphonic acid, naphthylphosphoric acid, glycerophosphonic acid, glycelophosphoric acid, p-nitrophenylphosphonic acid, p-nitrophenylphosphoric acid, p-methoxyphenylphosphonic acid, p-methoxyphenylphosphoric acid, p-hydroxyphenylphosphonic acid, p-hydroxyphenylphosphoric acid, p-tolylphosphonic acid, p-tolylphosphoric acid, p-acetylphenylphosphonic acid, p-acetylphenylphosphoric acid, p-cyanophenylphosphonic acid, p-cyanophenylphosphoric acid, m-chlorophenylphosphonic acid, m-chlorophenylphosphoric acid, methylphosphonic acid, methylenediphosphonic acid, ethylphosphonic acid, ethylenediphosphonic acid, 2-carboxyethylphosphonic acid, phosphonoacetic acid, 2-phenylethyl phosphonic acid 2-hydroxyethylphosphonic acid, 1-hydroxyethane-1,1-diphosphonic acid, aminohexylphosphoric acid, 2-methoxyethylphosphonic acid, 2-acetylethylphosphonic acid, glycine-N,N-bis(methylenephosphonic acid), phosphoserine, phosphothreonine, and pyridoxal phosphate.

Examples of the organic phophorus compound represented by formula (II) include phenylphosphinic acid, naphthylphosphinic acid, diphenylphosphinic acid, dimethylphosphinic acid, p-nitrophenylphosphinic acid, p-methoxyphenylphosphinic acid, p-hydroxyphenylphosphinic acid, p-tolylphosphinic acid, p-acetylphenylphosphinic acid, bisnitrophenylphosphoric acid, dioctylphosphate, diisopropylphosphate, dibutylphospate, dimethylphospate, diethylphosphate, di-2-ethylhexylphosphate, diphenylphosphate, methylphosphinic acid, ethylphosphinic acid, diethylphosphinic acid, 2-carboxyethylphosphonic acid, 2-phenylethylphosphinic acid, 2-hydroxyethylphosphinic acid, 2-methoxyethylphosphinic acid and 2-acetylethylphosphinic acid.

Among these compounds phenylphosphinic acid, phenylphosphoric acid, naphthylphosphonic acid, naphthylphosphoric acid, phenylphosphinic acid, diphenylphosphinic acid and naphthylphosphinic acid are more preferred.

Two or more of the organic phosphorus compound may be used in combination in the photoresist composition of the present invention.

In the present invention, the ratio of an organic phosphorus compound (c) to the resin (a) is 0.001 to 10 parts by weight, preferably 0.005 to 7 parts by weight and more preferably 0.01 to 5 parts by weight of the organic phosphoric acid compound per 100 parts by weight of the resin. A ratio of less than 0.001 part by weight notably lowers the adhesiveness and that exceeding 10 parts by weight reduces the residual layer rate and etching speed in wet etching.

In the present invention, a polyhydroxy compound can be added into the photoresist composition in order to further accelerate dissolution in a developing solution. Examples of preferred polyhydroxy compounds, include phenols, resorcin, fluoroglucine, 2,3,4-trihydroxybenzophenone, 2,3,4,4'-tetrahydroxybenzophenone, an acetone-pyrogallol condensation resin, and fluoroglucide. The preferred uppermost amount of the compounds is 50 parts by weight based on 100 parts by weight of the resin (a).

There can be exemplified as a solvent for dissolving the light-sensitive material and the resin (a) according to the present invention, ketones such as methyl ethyl ketone and cyclohexanone, alcohol ethers such as ethylene glycol monomethyl ether and ethylene glycol monoethyl ether, ethers such as dioxane and ethylene glycol dimethyl ether, cellosolve esters such as methylcellosolve acetate and ethylcellosolve acetate, fatty acid esters such as butyl acetate, methyl lactate, and ethyl lactate, halogenated hydrocarbons such as 1,1,2-trichloroethylene, and high polar solvents such as dimethylacetamide, N-methylpyrrolidone, dimethylformamide, and dimethylsulfoxide. These solvents can be used singly or in combination of plural solvents.

A dye, a plasticizer, an adhesive aid, and a surface active agent can be incorporated into the photoresist composition of the present invention, if desired, preferably in an amount of not more than 60 parts by weight based on the 100 parts by weight of the resin (a). Examples include a dye such as Methyl Violet and Malichite Green, a plasticizer such as stearic acid, an acetal resin, a phenoxy resin, and an alkyd resin, an adhesive aid such as an epoxy compound and chloromethylsilane, and a surface active agent such as nonylphenoxypoly(ethyleneoxy)) ethanol and octylphenoxypoly(ethyleneoxy) ethanol.

The above photoresist composition is coated on the surface of a substrate (for example, silicon, a silicon/silicon dioxide film, a silicon/silicon nitride film, aluminum, glass, glass/ITO (indium tin oxide, glass/chromium, glass/tantalum, glass/aluminum, a glass/silicon nitride film, glass/amorphous silicon, glass/tangusten, ceramics, copper, and others; the photoresist composition is coated on the material which is shown after the slash in the combination) used for manufacturing a precession integrated circuit element by a suitable coating method such as a spinner and a coater and after drying it is exposed through a prescribed mask and developed whereby a superior resist pattern can be obtained. The thickness of the layer of the photoresist composition is usually from about 0.2 to 5 μm.

Examples of the developing solution for the photoresist composition of the present invention include aqueous solutions of alkalis including inorganic alkalis such as sodium hydroxide, potassium hydroxide, sodium carbonate, sodium silicate, sodium metasilicate, and aqueous ammonia; primary amines such as ethylamine and n-propylamine; secondary amines such as diethylamine and di-n-butylamine; tertiary amines such as triethylamine and methyl diethylamine; alkanol-amines such as dimethylethanolamine and triethanolamine; quaternary ammonium salts, such as tetramethylammonium hydroxide and tetraethylammonium hydroxide; and cyclic amines such as pyrrole and piperidine.

Further, alcohols and surface active agents can also be added to the aqueous solutions of the above alkalis in a suitable amount.

The photoresist pattern thus formed can be used to suitably subject the substrate to wet etching.

Any conventional etching method can be used in the present invention.

Examples of the etching method according to the present invention include a dip method in which a substrate is dipped in an etching solution or a spray method in which an etching solution is sprayed from a spray nozzle to thereby subject a substrate to etching. The substrate may also be subjected to a prewetting treatment with pure water or pure water/supersonic wave and a hydrophilicity treatment with an oxygen plasma if desired.

Any of the solutions in which acid, alkali and a solvent for the surface material of the substrate each are contained as a primary component can be used as an etching solution (etchant) according to the present invention. Particularly, when there is used an etchant in which acids such as hydrochloric acid, nitric acid, phosphoric acid and hydrofluoric acid are contained as a primary component, a notable effect can be obtained.

For the etchant and temperature condition, a phosphoric acid/nitric acid/acetic acid series etchant (for example, 16/1/1 by weight: the same hereinafter) at 30° to 60° C. may be used when the substrate is aluminum or glass/aluminum, a hydrofluoric acid/nitric acid series etchant (for example, 1/20) at 10° to 30° C. may be used when the substrate is silicon, glass/tantalum, glass/amorphous silicon, or glass/polysilicon, and a hydrofluoric acid/antimony fluoride series etchant (for example, 1/6) at 10° to 30° C. may be used when the substrate is a silicon/silicon oxide film, a silicon/silicon nitride film, or a glass/silicon nitride film.

A surface active agent and others can be suitably added to these etchants and used.

The etching time is different according to the kind of substrate and processing condition, and it is preferably 1.1 to 2 times as long as the time (a just etching time) expended for removing a portion of a large area which is not covered with a resist with an etchant.

The substrate is preferably rinsed by a dip method or a spray method with pure water after etching.

EXAMPLES

The examples of the present invention are shown below but the present invention is not limited thereto. A percentage means % by weight unless otherwise indicated.

SYNTHETIC EXAMPLE 1 (Modified Silsesquioxane)

Aluminum chloride anhydrous 1.5 g and acetyl chloride 50 ml were combined in a 300 ml flask equipped with a stirrer, a thermometer and a dropping funnel and stirred. Then, a solution prepared by dissolving polyphenysilsesquioxane 5 g having a molecular weight of 7800 in acetyl chloride 50 ml was gradually dropped. The reaction was carried out while keeping the temperature at 25° C. Hydrogen chloride was generated as the reaction went on. After carrying out the reaction for three hours, the flask was cooled down and the content thereof was poured into ice and water. The mixture was stirred well to decompose aluminum chloride and a polymer precipitate was filtered off, followed by washing well with water and then drying in a vacuum drier.

SYNTHETIC EXAMPLE 2 (A Photo Acid Generating Agent)

Synthesis of 1-adamantanemethylbenzoate (a-1)

Dissolved in methylene chloride 120 ml were 1-adamantanemethanol 16.7 g (0.100 mole) and benzoic acid 12.3 g (0.100 mole), and 4-dimethylaminopyridine 1.3 g (0.011 mole) was added thereto. Further, a methylene chloride solution 50 ml of dicyclohexylcarbodimide 22.7 g (0.110 mole) was added while stirring at a room temperature over a period of 30 minutes. Thereafter, the stirring was continued for three hours.

A white solid matter deposited (dicyclohexylurea) was filtered off and after the filtrate was concentrated, it was purified using column chromatography (filler: silica gel; an eluting solution: hexane/ethyl acetate=4/1 by volume: the same hereinafter). A white powder thus obtained was recrystallized with methanol-water (10:10 by volume), whereby a white crystal 20.5 g was obtained. It was confirmed with NMR that this white crystal was 1-adamantanemethylbenzoate (yield: 76%).

SYNTHETIC EXAMPLE 3

Synthesis of 1,2,4-tris(adamantanemethyl) Benzoate (a-4)

Dissolved in methylene chloride 120 ml were 1-adamantanemethanol 25.1 g (0.15 mole) and trimellitic acid 10.5 g (0.050 mole), and 4-dimethylaminopyridine 2.0 g (0.017 mole) was added thereto. Further, a methylene chloride solution 70 ml of dicyclohexylcarbodimide 34.1 g (0.0165 mole) was added while stirring at room temperature over a period of 30 minutes. Thereafter, the stirring was continued for further three hours.

A white solid matter deposited (dicyclohexylurea) was filtered off and after the filtrate was concentrated, it was purified using column chromatography (filler: silica gel; an eluting solution: hexane/ethyl acetate=4/1). A white powder thus obtained was recrystallized with methanol-water (10:10 by volume), whereby a white crystal 23.9 g was obtained. It was confirmed with NMR that this white crystal was 1,2,4-tris(adamantanemethyl) benzoate (yield: 73%).

SYNTHETIC EXAMPLE 4

Synthesis of 1,2,4,5-tetrakis(adamantanemethyl) Benzoate (a-6)

Dissolved in methylene chloride 120 ml were 1-adamantanemethanol 25.1 g (0.16 mole) and pyromellitic acid anhydride 8.7 g (0.040 mole), and 4-dimethylaminopyridine 2.0 g (0.017 mole) was added thereto. Further, a methylene chloride solution 70 ml of dicyclohexylcarbodimide 34.1 g (0.0165 mole) was added while stirring at room temperature over a period of 30 minutes. Thereafter, the stirring was continued for three hours.

A white solid matter deposited (dicyclohexylurea) was filtered off and after the filtrate was concentrated, it was purified using column chromatography (filler: silica gel; an eluting solution: hexane/ethyl acetate=4/1). A white powder thus obtained was recrystallized with methanol-water (10:10 by volume), whereby a white crystal 23.7 g was obtained. It was confirmed with NMR that this white crystal was 1,2,4,5-tetrakis(adamantanemethyl) benzoate (yield: 70%).

SYNTHETIC EXAMPLE 5

Synthesis of p-(1-adamantanemethyl) Toluenesulfonate (a-12)

Dissolved in methylene chloride 120 ml were 1-adamantanemethanol 16.7 g (0.100 mole) and p-toluenesulfonic acid 19.0 g (0.100 mole), and 4-dimethylaminopyridine 1.3 g (0.011 mole) was added thereto. Further, a methylene chloride solution 50 ml of dicyclohexylcarbodimide 22.7 g (0.110 mole) was added while stirring at a room temperature over a period of 30 minutes. Thereafter, the stirring was continued for three hours.

A white solid matter deposited (dicyclohexylurea) was filtered off and after the filtrate was concentrated, it was purified using column chromatography (filler: silica gel; an eluting solution: hexane/ethyl acetate=4/1). A white powder thus obtained was recrystallized with methanol-water (10:10 by volume), whereby a white crystal 24.0 g was obtained. It was confirmed with NMR that this white crystal was p-(1-adamantanemethyl) toluenesulfonate (yield: 75%).

EXAMPLE 1

| | |
|---|---|
| Copolycondensation resin of m-cresol, p-cresol and formaldehyde (m/p mole ratio: 6:4, Mw = 9000, Mw/Mn = 6.0; Mn number average molecular weight) | 10.0 g |
| Condensation product of 1,2-naphthoquinonediazide-5-sulfonic acid chloride and 2,3,4-trihydroxybenzophenone(2/1 by mole) | 3.0 g |
| Phenylphosphoric acid | 0.01 g |
| Ethylcellosolve acetate | 142.0 g |

The above composition was filtrated with a micro filter of 0.2 μm to thereby prepare a photoresist composition. This photoresist composition was coated on a silicon/1 μm aluminum substrate with a spinner and dried on a hot plate at 90° C. for two minutes, whereby a resist film with a film thickness of 1.5 μm was obtained. This film was exposed with a reduction projection exposing equipment and then developed in a 2.38% tetrahydroxyammonium hydroxide aqueous solution for one minute, followed by washing with water for 30 seconds and then drying. After an enforced etching two times as much as a just etching was carried out in a phosphoric acid/nitric acid/acetic acid (16/1/1) series etchant at 40° C., a pattern was observed through a microscope to find that a pattern of 1 μm was formed without peeling off and that a good adhesiveness was shown.

EXAMPLE 2

| | |
|---|---|
| Copolycondensation resin of m-cresol, p-cresol and formaldehyde (m/p mole ratio: 6:4, Mw = 9000, Mw/Mn = 6.0) | 10.0 g |
| Condensation product of 1,2-naphthoquinonediazide-5-sulfonic acid chloride and 2,3,4,4-tetrahydroxybenzophenone (2/1 by mole) | 3.0 g |
| Phenylphosphonic acid | 0.1 g |
| Ethylcellosolve acetate | 142.0 g |

The above composition was filtrated with a micro filter of 0.2 μm and then subjected to coating, exposing, development and etching in the same manner as Example 1. It was found that a pattern of 1 μm was formed without peeling off and that a good adhesiveness was shown.

EXAMPLE 3

| | |
|---|---|
| Copolycondensation resin of m-cresol, p-cresol and formaldehyde (m/p mole ratio: 6:4, Mw = 9000, Mw/Mn = 6.0) | 10.0 g |
| Condensation product of 1,2-naphthoquinonediazide-5-sulfonic acid chloride and 3,3,3',3'-tetramethyl-1,1'-spirobi-indan-5,6,7,5',6',7'-hexol (2/1 by mole) | 3.0 g |
| n-Butylphosphonic acid | 0.2 g |
| Ethylcellosolve acetate | 142.0 g |

The above composition was filtrated with a micro filter of 0.2 μm and then subjected to coating, exposing, development and etching in the same manner as Example 1. It was found that a pattern of 1 μm was formed without peeling off and that a good adhesiveness was shown.

EXAMPLE 4

| | |
|---|---|
| Siloxane polymer obtained in Synthetic Example 1 | 10.0 g |
| Condensation product of 1,2-naphthoquinonediazide-5-sulfonic acid chloride and an o-novolak resin | 2.5 g |
| Benzylphosphonic acid | 0.3 g |
| Ethylcellosolve acetate | 142.0 g |

The above composition was filtrated with a micro filter of 0.2 μm and then subjected to coating, exposing, development and etching in the same manner as Example 1. It was found that a pattern of 1 μm was formed without peeling off and that a good adhesiveness was shown.

EXAMPLE 5

| | |
|---|---|
| Copolycondensation resin of m-cresol, p-cresol and formaldehyde (m/p mole ratio: 4:6, Mw = 4260, Mw/Mn = 2.6) | 10.0 g |
| Condensation product of 1,2-naphthoquinonediazide-5-sulfonic acid chloride and 3,3,3',3'-tetramethyl-1,1'-spirobi indan-5,6,7,5',6',7'-hexol (2.5/1 mol) | 3.0 g |
| Phenylphosphonic acid | 0.02 g |
| Ethylcellosolve acetate | 142.0 g |

The above composition was filtrated with a micro filter of 0.2 μm to thereby prepare a photoresist composition. This photoresist composition was coated on a glass/tantallum substrate with a spinner and dried on a hot plate at 100° C. for two minutes, whereby a resist film with a film thickness of 1.5 μm was obtained. This film was exposed with contact exposing equipment and then developed in a 2.38% tetrahydroxyammonium hydroxide aqueous solution for one minute, followed by washing with water for 30 seconds and then drying. After an enforced etching two times as much as a just etching was carried out in a hydrofluoric acid/nitric acid (1/20) series etchant at 21° C., a pattern was observed through a microscope to find that a pattern of 3 μm was formed without peeling off and that a good adhesiveness was shown.

EXAMPLE 6

| | |
|---|---|
| Acetone-pyrogallol resin | 10.0 g |
| Condensation product of 1,2-naphthoquinonediazide-5-sulfonic acid chloride and 3,3,3',3'-tetramethyl-1,1'-spirobi-indan-5,6,7,5',6',7'-hexol (2/1 by mol) | 3.0 g |
| 4-Methoxyphenylphosphonic acid | 0.2 g |
| Ethylcellosolve acetate | 142.0 g |

The above composition was filtrated with a micro filter of 0.2 μm and then subjected to coating, exposing, development and etching in the same manner as Example 5. It was found that a pattern of 3 μm was formed without peeling off and that a good adhesiveness was shown.

EXAMPLE 7

| Copolycondensation resin of m-cresol, p-cresol and formaldehyde (m/p mole ratio: 6:4, Mw = 9000, Mw/Mn = 6.0) | 10.0 g |
| Condensation product of 1,2-naphthoquinonediazide-5-sulfonic acid chloride and 2,3,4-trihydroxybenzophenone (2.5/1 by mol) | 3.0 g |
| n-Octylphosphonic acid | 0.5 g |
| Ethyl lactate | 142.0 g |

The above composition was filtrated with a micro filter of 0.2 μm to thereby prepare a photoresist composition. This photoresist composition was coated on a silicon/silicon nitride film substrate with a spinner and dried on a hot plate at 100° C. for two minutes, whereby a resist film with a film thickness of 1.5 μm was obtained. This film was exposed with a reduction projection exposing equipment and then developed in a 2.38% tetrahydroxyammonium hydroxide aqueous solution for one minute, followed by washing with water for 30 seconds and then drying. After an enforced etching two times as much as a just etching was carried out using a hydrofluoric acid/ammonium fluoride (1/6) series etchant at 21° C., a pattern was observed through a microscope to find that a pattern of 1 μm was formed without peeling off and that a good adhesiveness was shown.

EXAMPLE 8

| Polyhydroxystyrene resin (Mw = 9600) | 10.0 g |
| 4,4'-Diazidechalcone | 4.0 g |
| Benzylphosphonic acid | 0.2 g |
| Ethyl lactate | 142.0 g |

The above composition was filtrated with a micro filter of 0.2 μm and then subjected to coating, exposing, development and etching in the same manner as Example 7. It was found that a pattern of 3 μm was formed without peeling off and that a good adhesiveness was shown.

EXAMPLE 9

| Copolycondensation resin of m-cresol, p-cresol and formaldehyde (m/p mole ratio: 6:4, Mw = 9000, Mw/Mn = 6.0) | 10.0 g |
| 4,4'-Diazidechalcone | 4.0 g |
| 4-Tosyliminophenylphosphonic acid | 0.03 g |
| Ethyl lactate | 142.0 g |

The above composition was filtrated with a micro filter of 0.2 μm to thereby prepare a photoresist composition. This photoresist was coated on a silicon/silicon oxide film substrate with a spinner and dried on a hot plate at 100° C. for two minutes, whereby a resist film with a film thickness of 1.5 μm was obtained. This film was exposed with a reduction projection exposing equipment and then developed in a 2.38% tetrahydroxyammonium hydroxide aqueous solution for one minute, followed by washing with water for 30 seconds and then drying. After an enforced etching two times as much as a just etching was carried out using a hydrofluoric acid/ammonium fluoride (1/6) series etchant at 21° C., a pattern was observed through a microscope to find that a pattern of 1 μm was formed without peeling off and that a good adhesiveness was shown.

EXAMPLE 10

| Copolycondensation resin of m-cresol, p-cresol and formaldehyde (m/p mole ratio: 6:4, Mw = 9000, Mw/Mn = 6.0) | 7.0 g |
| Polyhydroxystyrene resin (Mw = 9600) | 3.0 g |
| Condensation product of 1,2-naphthoquinonediazide-5-sulfonic acid chloride and 2,3,4-trihydroxybenzophenone (3/1 by mol) | 3.0 g |
| n-Butylphosphonic acid | 0.2 g |
| Ethyl lactate | 142.0 g |

The above composition was filtrated with a micro filter of 0.2 μm and then subjected to coating, exposing, development and etching in the same manner as Example 9. It was found that a pattern of 1 μm was formed without peeling off and that a good adhesiveness was shown.

EXAMPLES 11 TO 22

The compounds of the present invention prepared in the Synthetic Examples 2 to 5 were used to prepare the resists. The compositions therefor are shown in Table 1. These resist compositions were filtrated with a micro filter of 0.2 μm and then subjected to coating, exposing, development and etching in the same manner as Example 1. It was found that a pattern of 1 μm was formed without peeling off and that a good adhesiveness was shown.

EXAMPLES 23 AND 24

A t-butoxycarbonyloxystyrene polymer and a t-butoxycarbonyloxy-α-methylstyrene polymer were synthesized according to the method described in U.S. Pat. No. 4,491,628 and the two component series positive type resists were prepared. The compositions therefor are shown in Table 1. These resist compositions were filtrated with a micro filter of 0.2 μm and then subjected to coating, exposing, development and etching in the same manner as Example 5. It was found that a pattern of 3 μm was formed without peeling off and that a good adhesiveness was shown.

EXAMPLES 25 AND 26

Di-t-butyl terephthalate, and 4-t-butoxy-p-biphenyl were used as an anti-dissolution agent to prepare the three component series positive type resists. The compositions therefor are shown in Table 1. These resist compositions were filtrated with a micro filter of 0.2 μm and then subjected to coating, exposing, development and etching in the same manner as Example 7. It was found that a pattern of 1 μm was formed without peeling off and that a good adhesiveness was shown.

TABLE 1

Compositions of the photoresist solutions

| Example | Alkali soluble resin | Photo acid generating agent | Anti-dissolution agent | Organic phosphorus compound | | Solvent* |
|---|---|---|---|---|---|---|
| 11 | NOV | 1.5 g TPSFA | 0.1 g (a-1) | 0.8 g Phenylphosphonic acid | 0.001 g | 6 g |
| 12 | NOV | 1.5 g TPSFS | 0.1 g (a-1) | 0.8 g Phenylphosphonic acid | 0.002 g | 6 g |
| 13 | NOV | 1.5 g DPIPP | 0.1 g (a-1) | 0.8 g Phenylphosphonic acid | 0.001 g | 6 g |
| 14 | NOV | 1.5 g TPSFA | 0.1 g (a-4) | 0.8 g n-Buylphosphonic acid | 0.008 g | 6 g |
| 15 | NOV | 1.5 g TPSFA | 0.1 g (a-6) | 0.8 g Phenylphosphonic acid | 0.001 g | 6 g |
| 16 | NOV | 1.5 g TPSFA | 0.1 g (a-12) | 0.8 g Phenylphosphonic acid | 0.002 g | 6 g |
| 17 | PVP | 1.5 g TPSFA | 0.1 g (a-1) | 0.8 g Phenylphosphonic acid | 0.001 g | 6 g |
| 18 | PVP | 1.5 g TPSFA | 0.1 g (a-4) | 0.8 g n-Buylphosphonic acid | 0.008 g | 6 g |
| 19 | PVP | 1.5 g TPSFA | 0.1 g (a-6) | 0.8 g Benzylphosphonic acid | 0.001 g | 6 g |
| 20 | PVP | 1.5 g TPSFA | 0.1 g (a-12) | 0.8 g Benzylphosphonic acid | 0.002 g | 6 g |
| 21 | NOV | 1.5 g DMDS | 0.1 g (a-6) | 0.8 g Benzylphosphonic acid | 0.001 g | 6 g |
| 22 | NOV | 1.5 g DMDS | 0.1 g (a-6) | 0.8 g n-Hexylphosphonic acid | 0.008 g | 6 g |
| 23 | TBOCS | 1.5 g TPSFA | 0.2 g — | Phenylphosphonic acid | 0.001 g | 5 g |
| 24 | TBAMS | 1.5 g TPSFA | 0.2 g — | Phenylphosphonic acid | 0.002 g | 5 g |
| 25 | NOV | 1.5 g TPSFA | 0.1 g DTBTP | 0.8 g Phenylphosphonic acid | 0.001 g | 6 g |
| 26 | NOV | 1.5 g TPSFA | 0.1 g TBPBP | 0.8 g n-octylphosphonic acid | 0.008 g | 6 g |

*Solvent: diethylene glycol dimethyl ether

TABLE 2

Abbreviations used in Table 1

Polymer

| | |
|---|---|
| NOV: | novolak resin, m/p = 45/55 (weight average molecular weight: 6,000) |
| PVP: | p-hydroxystyrene polymer (number average molecular weight: 9,600) |
| TBOCS: | t-butoxycarbonyloxystyrene polymer (number average molecular weight: 21,600) |
| TBAMS: | t-butoxycarbonyloxy-α-methylstyrene polymer (number average molecular weight: 46,900) |

Photo acid generating agent

TPSFA: triphenylphosphonium hexafluoroantimonate
TPSFS: triphenylphosphonium trifluoromethylsulfonate
DPIFP: diphenyliodonium hexafluorosulfonate
DMDS: 4,4'-dimethoxyphenyldisulfone Anti-dissolution compound DTBTP: di-t-butyl terephthalate
TBPBP: 4-t-butoxy-p-biphenyl

EXAMPLE 27

| | |
|---|---|
| Methyl methacrylate-methacrylic acid resin (mole ratio: 85:15, limiting viscosity in methyl ethyl ketone at 30° C.: 0.166) | 6.2 g |
| Pentaerythritol hexacrylate | 3.8 g |
| 4-[4-N,N'-di(ethoxycarbonylmethyl)amino-phenyl]4,6-bis(trichloromethyl)-s-triazine | 0.5 g |
| Diphenylmethylphosphonic acid | 0.02 g |
| Ethyl cellosolve | 70.0 g |

The above composition was filtrated with a micro filter of 0.2 μm and then subjected to coating, exposing, development and etching in the same manner as Example 9. It was found that a pattern of 1 μm was formed without peeling off and that a good adhesiveness was shown.

COMPARATIVE EXAMPLES 1 TO 27

The etchings and evaluations were carried out in the same compositions as those in the respective examples except that the organic phosphorus compounds were removed from the compositions. The patterns of 5 μm in Comparative Examples 1 to 4, 7 to 22 and 25 to 26, and the patterns of 15 μm in Comparative Examples 5, 6, 23, 24 and 27 lost adhesiveness and the resist films were peeled off.

Effects of the Invention

The photoresists of the present invention have the excellent resolution, sensitivity, developability, heat durability, and adhesiveness and can favorably be used as a photoresist for a fine processing.

While the invention has been described in detail and with reference to specific embodiments thereof, it will be apparent to one skilled in the art that various changes and modifications can be made therein without departing from the spirit and scope thereof.

What is claimed is:

1. A photoresist composition comprising in admixture:
   (a) an alkali soluble resin or a resin having anti-alkali dissolution groups in the molecules thereof,
   (b) a 1,2-quinonediazide light-sensitive compound, and
   (c) at least one organic compound selected from the group consisting of organic phosphorus acid compounds and esters thereof in an amount of 0.001 to 10% by weight based on the weight of the resin, wherein said organic compound (c) is selected from the group consisting of compounds represented by formulae (I) and (II):

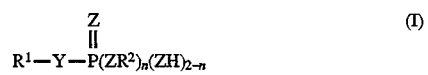

wherein n represents 1 or 2, $R^1$ represents an alkyl group, an alkoxyl group, an aryl group, an aryloxy group, an acyl group, or an acyloxy group, $R^2$ and $R^3$ each represents a hydrogen atom or an alkyl group, an aryl group, or an acyl group, Y represents a single bond, an oxygen atom or a sulfur atom, and Z represents an oxygen atom or a sulfur atom, and said organic compound may be a salt of a metal or ammonium.

2. The photoresist composition of claim 1, wherein said resin is at least one alkali soluble resin selected from the group consisting of a novolak resin, an acetone-pyrogallol resin, polyhydroxystyrene, a styrene-maleic acid anhydride copolymer, modified polysilsesquioxane modified to an alkali soluble type by a Friedel-Crafts reaction, and a carboxyl group-containing methacrylate series resin and a derivative thereof.

3. The photoresist composition of claim 1, wherein said resin having anti-alkali dissolution groups in the molecules thereof is at least one resin selected from the group consisting of a t-butoxycarbonyloxystyrene polymer and a t-butoxycarbonyloxy-α-methylstyrene polymer.

4. The photoresist composition of claim 1, wherein said 1,2-quinonediazide is in an amount of from 5 to 100 parts by weight based on 100 parts by weight of said resin.

5. The photoresist composition of claim 1, wherein said organic compound (c) is in an amount of from 0.005 to 7.0 by weight based on 100 parts by weight of said resin.

6. The photoresist composition of claim 1, wherein said organic compound (c) is in an amount of from 0.01 to 5.0 parts by weight based on 100 parts by weight of said resin.

7. The photoresist composition of claim 1, wherein said organic phosphorus acid compounds are an organic phosphoric acid compound, an organic phosphorous acid compound, an organic phosphonic acid compound and an organic phosphinic acid compound.

8. The photoresist composition of claim 1, wherein said light-sensitive compound is in an amount of 0.001 to 100 parts by weight based on 100 parts by weight of said resin.

9. The photoresist composition of claim 1, wherein said organic compound (c) represented by formula (I) is selected from the group consisting of phenylphosphonic acid, phenylphosphoric acid, naphthylphosphonic acid, naphthylphosphoric acid, glycerophosphonic acid, glycerophosphoric acid, p-nitrophenylphosphonic acid, p-nitrophenylphosphoric acid, p-methyoxyphenylphosphonic acid, p-methoxyphenylphosphoric acid, p-hydroxyphenylphosphonic acid, p-hydroxyphenylphosphoric acid, p-tolylphosphonic acid, p-tolylphosphoric acid, p-acetylphenylphosphonic acid, p-acetylphenylphosphoric acid, p-cyanophenylphosphonic acid, p-cyanophenylphosphoric acid, m-chlorophenylphosphonic acid, m-chlorophenylphosphoric acid, methylphosphonic acid, methylenediphosphonic acid, ethylphosphonic acid, ethylenediphosphonic acid, 2-carboxyethylphosphonic acid, phosphonoacetic acid, 2-phenylethyl phosphonic acid, 2-hydroxyethylphosphonic acid, 1-hydroxyethane-1,1-diphosphonic acid, aminohexylphosphoric acid, 2-methoxyethylphosphonic acid, 2-acetylethylphosphonic acid, glycine-N,N-bis(methylenephosphonic acid), phosphoserine, phosphothreonine, and pyridoxal phosphate.

10. The photoresist composition of claim 1, wherein said organic compound (c) represented by formula (II) is selected from the group consisting of phenylphosphinic acid, naphthylphosphinic acid, diphenylphosphinic acid, dimethylphosphinic acid, p-nitrophenylphosphinic acid, p-methoxyphenylphosphinic acid, p-hydroxyphenylphosphinic acid, p-tolylphosphinic acid, p-acetylphenylphosphinic acid, bisnitrophenylphosphoric acid, dioctylphosphate, diisopropylphosphate, dibutylphosphate, dimethylphosphate, diethylphosphate, di-2-ethylhexylphosphate, diphenylphosphate, methylphosphinic acid, ethylphosphinic acid, diethylphosphinic acid, 2-carboxyethylphosphonic acid, 2-phenylethylphosphinic acid, 2-hydroxyethylphosphinic acid, 2-methoxyethylphosphinic acid, and 2-acetylethylphosphinic acid.

11. A photoresist comprising a substrate having coated on the surface thereof a photoresist composition comprising in admixture:

(a) an alkali soluble resin or a resin having anti-alkali dissolution groups in the molecules thereof, (b) a 1,2-quinonediazide light-sensitive compound, and (c) at least one organic compound selected from the group consisting of organic phosphorus acid compounds and esters thereof in an amount of 0.001 to 10% by weight based on the weight of the resin, wherein said organic compound (c) is selected from the group consisting of compounds represented by formulae (I) and (II):

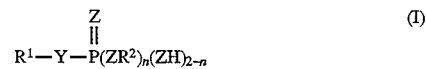

wherein n represents 1 or 2, $R^1$ represents an alkyl group, an alkoxyl group, an aryl group, an aryloxy group, an acyl group, or an acyloxy group, $R^2$ and $R^3$ each represents a hydrogen atom or an alkyl group, an aryl group, or an acyl group, Y represents a single bond, an oxygen atom or a sulfur atom, and Z represents an oxygen atom or a sulfur atom, and said organic compound may be a salt of a metal or ammonium.

12. The photoresist of claim 11, wherein said resin is at least one alkali soluble resin selected from the group consisting of a novolak resin, an acetone-pyrogallol resin, polyhydroxystyrene, a styrene-maleic acid anhydride copolymer, modified polysilsesquioxane modified to an alkali soluble type by a Friedel-Crafts reaction, and a carboxy group-containing methacrylate series resin and a derivative thereof.

13. The photoresist of claim 11, wherein said resin having anti-alkali dissolution groups in the molecules thereof is at least one resin selected from the group consisting of a t-butoxycarbonyloxystyrene polymer and a t-butoxycarbonyloxy-α-methylstyrene polymer.

14. The photoresist of claim 11, wherein said 1,2-quinonediazide is in an amount of from 5 to 100 parts by weight based on 100 parts by weight of said resin.

15. The photoresist of claim 11, wherein said organic compound (c) is in an amount of from 0.005 to 7.0 by weight based on 100 parts by weight of said resin.

16. The photoresist of claim 11, wherein said organic compound (c) is in an amount of from 0.01 to 5.0 parts by weight based on 100 parts by weight of said resin.

17. The photoresist of claim 11, wherein said organic phosphorus acid compounds are an organic phosphoric acid compound, an organic phosphorous acid compound, an organic phosphonic acid compound and an organic phosphinic acid compound.

18. The photoresist of claim 11, wherein said light-sensitive compound is in an amount of 0.001 to 100 parts by weight based on 100 parts by weight of said resin.

19. The photoresist of claim 11, wherein said organic compound (c) represented by formula (I) is selected from the group consisting of phenylphosphonic acid, phenylphosphoric acid, naphthylphosphonic acid, naphthylphosphoric acid, glycerophosphonic acid, glycerophosphoric acid, p-nitrophenylphosphonic acid, p-nitrophenylphosphoric acid, p-methyoxyphenylphosphonic acid, p-methoxyphenylphosphoric acid, p-hydroxyphenylphosphonic acid, p-hydroxyphenylphosphoric acid, p-tolylphosphonic acid, p-tolylphosphoric acid, p-acetylphenylphosphonic acid, p-acetylphenylphosphoric acid, p-cyanophenylphosphonic acid, p-cyanophenylphosphoric acid, m-chlorophenylphosphonic acid, m-chlorophenylphosphoric acid, methylphosphonic acid, methylenediphosphonic acid, ethylphosphonic acid, ethylenediphosphonic acid, 2-carboxyethylphosphonic acid, phosphonoacetic acid, 2-phenylethyl phosphonic acid, 2-hydroxyethylphosphonic acid, 1-hydroxyethane-1,1-diphosphonic acid, aminohexylphosphoric acid, 2-methoxyethylphosphonic acid, 2-acetylethylphosphonic acid, glycine-N,N-bis(methylenephosphonic acid), phosphoserine, phosphothreonine, and pyridoxal phosphate.

20. The photoresist of claim 11, wherein said organic compound (c) represented by formula (II) is selected from the group consisting of phenylphosphinic acid, naphthylphosphinic acid, diphenylphosphinic acid, dimethylphosphinic acid, p-nitrophenylphosphinic acid, p-methoxyphenylphosphinic acid, p-hydroxyphenylphosphinic acid, p-tolylphosphinic acid, p-acetylphenylphosphinic acid, bisnitrophenylphosphoric acid, dioctylphosphate, diisopropylphosphate, dibutylphosphate, dimethylphosphate, diethylphosphate, di-2-ethylhexylphosphate, diphenylphosphate, methylphosphinic acid, ethylphosphinic acid, diethylphosphinic acid, 2-carboxyethylphosphonic acid, 2-phenylethylphosphinic acid, 2-hydroxyethylphosphinic acid, 2-methoxyethylphosphinic acid, and 2-acetylethylphosphinic acid.

21. The photoresist of claim 11, wherein the material forming the surface of said substrate is selected from the group consisting of silicon, silicon dioxide, silicon nitride, aluminum, glass, ITO, chromiun, tantalum, amorphous silicon, tungsten, ceramics, and copper.

\* \* \* \* \*